United States Patent [19]

Arendsen

[11] 4,226,877
[45] Oct. 7, 1980

[54] PYRAZOLES ACTIVE IN THE CENTRAL NERVOUS SYSTEM

[75] Inventor: David L. Arendsen, Libertyville, Ill.

[73] Assignee: Abbott Laboratories, North Chicago, Ill.

[21] Appl. No.: 39,015

[22] Filed: May 14, 1979

Related U.S. Application Data

[63] Continuation-in-part of Ser. No. 881,319, Feb. 27, 1978, abandoned.

[51] Int. Cl.² .................. A61K 31/415; C07D 403/12
[52] U.S. Cl. ............................... 424/273 P; 548/364; 548/374
[58] Field of Search ............................... 548/364, 374; 424/273 P

[56] References Cited

U.S. PATENT DOCUMENTS

| 3,875,128 | 4/1975 | Bretschneider et al. | 548/374 |
| 3,953,467 | 4/1976 | Fujimura et al. | 548/374 |
| 4,069,330 | 1/1978 | Berger et al. | 548/374 |

Primary Examiner—Alan L. Rotman
Assistant Examiner—Natalia Harkaway
Attorney, Agent, or Firm—Robert L. Niblack; Gildo E. Fato

[57] ABSTRACT

Disclosed are pyrazoles of the formula

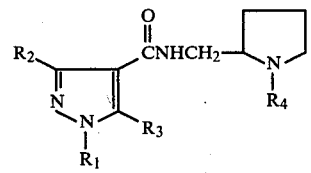

wherein $R_1$ is hydrogen, lower alkyl, or phenyl, $R_2$ is hydrogen or lower alkyl, $R_3$ is alkoxy or hydroxy, $R_4$ is lower alkyl, and the pharmaceutically acceptable acid addition salts thereof. The compounds are useful primarily as antipsychotic agents. As an example, they exhibit central nervous system activity as antischizophrenic agents.

9 Claims, No Drawings

PYRAZOLES ACTIVE IN THE CENTRAL NERVOUS SYSTEM

This application is a continuation-in-part application of application Ser. No. 881,319, filed Feb. 27, 1978, now abandoned.

DETAILED DESCRIPTION OF THE INVENTION

This invention relates to pyrazoles which are useful primarily as antipsychotic agents. The compounds included in the invention can be represented by the following structural formula

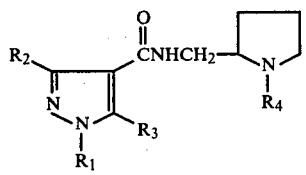

wherein $R_1$ is hydrogen, lower alkyl, or phenyl, $R_2$ is hydrogen or lower alkyl, $R_3$ is alkoxy or hydroxy and $R_4$ is lower alkyl.

The compounds of this invention exhibit central nervous system activity as antischizophrenic agents. The antischizophrenic activity is evident at dosages of from 1 to 80 milligrams per kilogram (mg/kg) of body weight when administered orally and from 0.2 to 5.0 mg/kg of body weight when administered intraperitoneally (i.p.).

The compounds of the present invention can be made by condensing the appropriate β-ketoester with a substituted hydrazine in ethanol. Using the Vilsmeier-Haack reaction (Ber. 60, 119, 1927), the resulting pyrazolone is converted to the 5-chloro-4-pyrazole carboxaldehyde which is oxidized with permanganate to produce a 5-alkoxy-4-pyrazole carboxylic acid. With the aid of N,N'-carbonyl-diimidazole, the carboxylic acids are condensed with an appropriate aminopyrrolidine to produce the described amides.

A general scheme for preparation of the described compounds can be represented as follows. In those compounds wherein $R_3$ is hydroxy, water is used in place of an alcohol in Step 3.

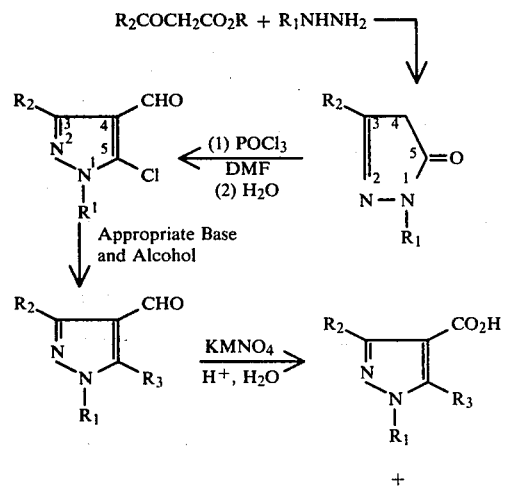

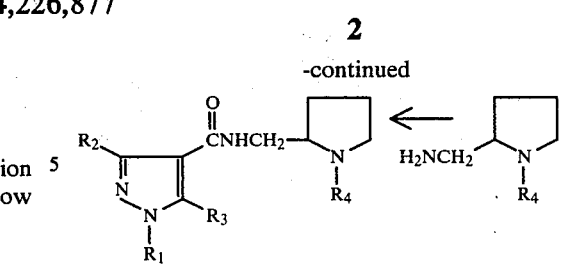

The following examples are presented to further illustrate the present invention.

EXAMPLE 1

1,3-dimethyl-5-methoxy-4-pyrazole carboxylic acid 2.5 g (0.0162 mole) of 1,3-dimethyl-5-methoxy-4-pyrazole carboxaldehyde (prepared as described in Khim. Farm. Zh, 4, 19 (1970) [CA, 73, 3844 w, (1970)] was dissolved in a solution containing 50 ml of water, 2 ml of acetic acid and 0.6 ml of acetone. 2.56 g (0.0162 mole) of potassium permanganate was added in several portions. The reaction was stirred for 3 hours before decomposing the excess potassium permanganate with 3 ml of methanol and then made alkaline with ammonium hydroxide, heated on the steam bath for ½ hour, and filtered. The filtrate was evaporated to approximately 30 ml of solution which was then acidified to pH4 with concentrated HCl. The solid was then collected. 1.6 g (58% yield) was obtained, m.p. 179°–180° C., white solid.

Infrared and nmr data confirm the structure. Analysis calculated for $C_7H_{10}N_2O_3$: C, 49.40; H, 5.92; N, 16.46; Found: C, 49.40; H, 6.03; N, 16.65.

EXAMPLE 2

N-[(1-ethyl-2-pyrrolidinyl)methyl]-5-methoxy-1,3-dimethylpyrazole-4-carboxamide 3.1 g (0.0178 mole) of 1,3-dimethyl-5-methoxy-4-pyrazole carboxylic acid was dissolved in 15 ml of dry N,N-dimethylformamide. Then 3.18 g (0.0196 mole) of 1,1'-carbonyl-diimidazole was added. The reaction mixture was stirred for one hour. A solution of 2.28 g (0.0178 mole) of 2-(aminomethyl)-1-ethylpyrrolidine in 10 ml of dry tetrahydrofuran was added dropwise with stirring over ½ hour. The reaction was then stirred overnight at room temperature and the solvent evaporated under vacuum (1 mm) and a water bath (60° C.). The resultant oil was then taken up in chloroform, washed with a saturated solution of sodium chloride, dried over sodium sulfate and evaporated. 4.5 g of amber colored oil (90% yield) was obtained.

Infrared and nmr data confirm the structure. Analysis calculated for $C_{14}H_{26}N_4O.\frac{1}{2}H_2O$: C, 61.06; H, 9.88; N, 20.35; Found: C, 61.67; H, 9.67; N, 20.17.

The following compounds can be prepared as indicated.

5-Chloro-3-methyl-1-phenyl-4-pyrazole carboxaldehyde can be prepared according to the method described in Ann. Chem., 681, 105 (1965).

5-Methoxy-3-methyl-1-phenyl-4-pyrazole carboxaldehyde can be prepared by a method similar to the procedures described in Khim. Farm. Zh. 4, 19 (1970) [CA, 73, 3844 w, (1970)] simple distillation. b.p. 122–130 (0.05 mm) (26% yield) IR and nmr data were consistent with the structure.

5-Methoxy-3-methyl-1-phenyl-4-pyrazole carboxylic acid can be prepared by a method similar to the procedures of Example 1. m.p. 160°–161° C. (28% yield) IR and nmr data were consistent with the structure. Analysis calculated for $C_{12}H_{12}N_2O_3$; C, 62.062; H, 5.208; N, 12.062; Found: C, 62.10; H, 5.23; N, 12.14.

N-[(1-Ethyl-2-pyrrolidinyl) methyl]-5-methoxy-3-methyl-1-phenyl pyrazole-4-carboxamide can be prepared by a method similar to the procedure of Example 2. A light amber oil was obtained (14% yield). IR and nmr data were consistent with the structure. Analysis calculated for $C_{19}H_{26}N_4O_2$: C, 66.64; H, 7.653; N, 16.36; Found: C, 66.72; H, 7.96; N, 15.37.

1-Isopropyl-3-methyl-5-pyrazolone can be prepared according to the method described in U.S. Pat. No. 3,558,605.

5-Chloro-1-isopropyl-3-methyl-4-pyrazole carboxaldehyde can be prepared by a method similar to the procedure described in Ann. Chem., 681, 105, (1965). Kugelrohr distilled, 80°–85° C. at 0.01 mm. white solid was obtained, m.p. 110°–112° C. (56% yield). Infrared and nmr data were consistent with the structure. Analysis calculated for $(C_8H_{11}ClN_2O)$; C, 51.483; H, 5.941; N, 15.008; Found: C, 51.22; H, 6.01; N, 15.10.

1-Isopropyl-5-methoxy-3-methyl-4-pyrazole carboxaldehyde can be prepared by a method similar to the procedure described in Khim. Farm. Zh. 4, 19 (1970) [CA, 73, 3844 w, (1970)]. Amber semi-solid (34% yield). Infrared and nmr data were consistent with the structure.

1-Isopropyl-5-methoxy-3-methyl-4-pyrazole carboxylic acid prepared by the procedure of Example 1. White solid was obtained (34% yield). Infrared and nmr data were consistent with the structure.

N-[(1-Ethyl-2-pyrrolidinyl) methyl]-1-isopropyl-5-methoxy-3-methylpyrazole-4-carboxamide is prepared by a method similar to the procedure of Example 2. Amber oil is obtained (25% yield). Infrared and nmr data were consistent with the desired structure. Analysis calculated for $C_{16}H_{28}N_4O_2$; C, 62.31; H, 9.150; N, 18.165; Found: C, 61.88; H, 9.41; N, 18.15.

3-Isopropyl-1-methyl-5-pyrazolone is prepared according to the method described in U.S. Pat. No. 3,558,605.

5-Chloro-3-isopropyl-1-methyl-4-pyrazole carboxaldehyde is prepared by the procedure described in Ann. Chem. 681, 105, 1965. Simple distillation, b.p. 84°–86° C., (0.11 mm) (35% yield). Infrared and nmr data were consistent with the desired structure. Analysis calculated for $C_8H_{11}ClN_2O$: C, 51.483; H, 5.941; N, 15.008; Found: C, 51.01; H, 6.15; N, 15.35.

3-Isopropyl-5-methoxy-1-methyl-4-pyrazole carboxaldehyde is prepared by the procedure described in Khim. Farm. Zh. 4, 19 (1970) [CA, 73, 3844 w, (1970)]. A light yellow oil (65% yield) is obtained. Kngelrohr distillation 60° C. (0.1 mm). Infrared and nmr data are consistent with the structure.

3-Isopropyl-5-methoxy-1-methyl 4-pyrazole carboxylic acid is prepared by the procedure of Example 1. White solid (45% yield) is obtained. Infrared and nmr data are consistent with the structure.

N[(1-Ethyl-2-pyrrolidinyl) methyl]-3-isopropyl-5-methoxy-1-methylpyrazole 4-carboxamide is prepared by the procedure of Example 2. Amber oil (23% yield) is obtained. Infrared and nmr data were consistent with the structure. Analysis Calculated for $C_{16}H_{28}N_4O_2$: C, 62.31; H, 9.150; N, 18.165; Found: C, 61.91; H, 9.39; N, 18.87.

EXAMPLE 3

Effect of Drug Compounds on Brain Level of Homovanillic Acid (HVA)

In testing for the effectiveness of the present drug compounds on the brain level of homovanillic acid (HVA), the drugs were administered intraperitoneally to male Long Evans rats (Simonsen) usually as aqueous solutions but in certain cases as suspensions in 0.5% methocel in 0.9% saline. The standard testing dose was 0.15 moles/kg body weight. The test and control groups consisted of 3–5 and 5 animals, respectively. The analyses were performed on brains (minus cerebella) removed two or three hours later. In the analyses, standard extraction and fluorimetric methods were used. The results of the analysis are set forth in the table below.

In the results, the level of brain HVA in each test group is expressed as a ratio to the level of HVA in an accompanying control group that was injected with either a 0.9% saline or a 0.5% solution of methocel. Even though ratios of less than 1.3 usually have statistical significance, only ratios greater than 1.6 are considered to be of practical significance for the pharmacological classification of drugs.

Antipsychotic agents increase the synthesis and release of dopamine which is converted to HVA. The HVA level is therefore a measure of dopamine release. The effect of the described compounds on the HVA level in rats is summarized in Table I.

TABLE I

Effect of the Described Compounds on the Level of Homovanillic Acid (HVA) in the Brain of Rats

| Compound | | | | | HVA Level in | HVA Level; |
|---|---|---|---|---|---|---|
| $R_1$ | $R_2$ | $R_3$ | $R_4$ | Dose | Control Group | Compound : Control Ratio |
| I $CH_3$ | $CH_3$ | $OCH_3$ | $CH_2CH_3$ | 0.15 | 1 | 4.0 |
| II $CH(CH_3)_2$ | $CH_3$ | $OCH_3$ | $CH_2CH_3$ | 0.15 | 1 | 1.8 |
| III $CH_3$ | $CH(CH_3)_2$ | $OCH_3$ | $CH_2CH_3$ | 0.15 | 1 | 1.0 |
| IV $CH(CH_3)_2$ | $CH_3$ | OH | $CH_2CH_3$ | 0.15 | 1 | 2.2 |
| V (phenyl) | $CH_3$ | $OCH_3$ | $CH_2CH_3$ | 0.15 | 1 | 3.3 |
| Sulpiride | | | | 0.15 | 1 | 3.0 |
| Chlorpromazine | | | | 0.03 | 1 | 3.9 |

EXAMPLE 4

Methamphetamine Antagonism Test

The second test for identifying potential antipsychotic properties was the rat methamphetamine antagonism test.

Male, Long-Evans, black hooded rats, weighing between 100 and 150 grams, were administered the compounds at oral doses of 5, 20, and 80 mg/kg. Three rats were tested at each dose level. Placebo controls received a volume dose of the 0.5% carboxymethylcellulose vehicle. One hour after drug administration, the animals received methamphetamine at an intraperitoneal dose of 1 mg/kg and were placed in individual test chambers equipped with photocells (Lehigh Valley, Model 1497). Antagonism of methamphetamine-induced hyperactivity was recorded as digital counts received from the photocells at one and two hour intervals.

The drug data were compared to placebo control values to identify statistically significant differences using a one-way analysis of variance computer program. ED50's were calculated by the method of Litchfield and Wilcoxin (J. Pharmacol. Exper. Therap.: 96:99, 1949).

The results are summarized in Table 2.

TABLE 2

Effectiveness of Claimed Compounds on Inhibiting Methamphetamine Antagonism in Rats

| Compound | Dose | % Change From Placebo Control | $ED_{50}$ MG/KG |
|---|---|---|---|
| I | 5 | −9 | 44 |
|  | 20 | −35 |  |
|  | 80 | −60 |  |
| II | 5 | −16 | >80 |
|  | 20 | −13 |  |
|  | 80 | −16 |  |
| III | 5 | −31 | >80 |
|  | 20 | −33 |  |
|  | 80 | −12 |  |
| IV | 5 | +35 | >80 |
|  | 20 | +28 |  |
|  | 80 | −18 |  |
| V | 5 | −23 | 23.5 |
|  | 20 | −32 |  |
|  | 80 | −81 |  |
| Sulpiride | 5 | +27 | >80 |
|  | 20 | +21 |  |
|  | 80 | 0 |  |
| Chlorpromazine | 5 | +10 | 15 |
|  | 10 | −40 |  |
|  | 20 | −74 |  |

What is claimed is:

1. A compound of the formula

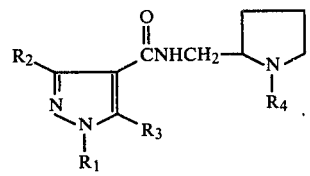

wherein $R_1$ is hydrogen, lower alkyl, or phenyl, $R_2$ is hydrogen or lower alkyl, $R_3$ is lower alkoxy or hydroxy, and $R_4$ is lower alkyl, provided the compound wherein $R_2$ is isopropyl when $R_1$ is methyl, $R_3$ is methoxy and $R_4$ is ethyl is excluded, and the pharmaceutically acceptable acid addition salts thereof.

2. The compound of claim 1 wherein $R_1$ and $R_2$ are methyl, $R_3$ is methoxy, and $R_4$ is ethyl.

3. The compound of claim 1 wherein $R_1$ is phenyl, $R_2$ is methyl, $R_3$ is methoxy, and $R_4$ is ethyl.

4. The compound of claim 1 wherein $R_1$ is isopropyl, $R_2$ is methyl, $R_3$ is methoxy, and $R_4$ is ethyl.

5. The compound of claim 1 wherein $R_1$ is isopropyl, $R_2$ is methyl, $R_3$ is hydroxy, and $R_4$ is ethyl.

6. A method of treating schizophrenia in mammals which method comprises administering to a mammal in need of such treatment an effective amount of a compound of the formula

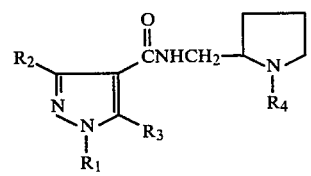

wherein $R_1$ is hydrogen, lower alkyl, or phenyl, $R_2$ is hydrogen or lower alkyl, $R_3$ is lower alkoxy or hydroxy, and $R_4$ is lower alkyl, provided the compound wherein $R_2$ is isopropyl when $R_1$ is methyl, $R_3$ is methoxy and $R_4$ is ethyl is excluded, or a pharmaceutically acceptable acid addition salt thereof.

7. The method of claim 6 wherein $R_1$ and $R_2$ are each lower alkyl, $R_3$ is methoxy or hydroxy, and $R_4$ is ethyl.

8. The method of claim 6 wherein $R_1$ and $R_2$ are each methyl or isopropyl, $R_3$ is methoxy or hydroxy, and $R_4$ is ethyl.

9. A composition for the treatment of schizophrenia, said composition comprising an effective amount of a compound of the formula

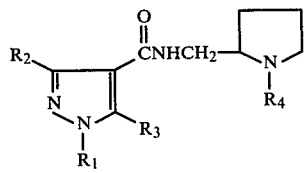

wherein $R_1$ is hydrogen, lower alkyl, or phenyl, $R_3$ is lower alkoxy or hydroxy, and $R_4$ is lower alkyl, provided the compound wherein $R_2$ is isopropyl when $R_1$ is methyl, $R_3$ is methoxy and $R_4$ is ethyl is excluded, or a pharmaceutically acceptable acid addition salt thereof, and a pharmaceutically acceptable carrier.